United States Patent
Kraemer et al.

(10) Patent No.: US 9,186,104 B2
(45) Date of Patent: Nov. 17, 2015

(54) INSTRUMENTS AND SYSTEM FOR PRODUCING A SAMPLE OF A BODY FLUID AND FOR ANALYSIS THEREOF

(71) Applicant: Roche Diagnostics Operations, Inc., Indianapolis, IN (US)

(72) Inventors: Uwe Kraemer, Ilvesheim (DE); Volker Zimmer, Morbach (DE); Wolfgang Roedel, Heidelberg (DE); Hans List, Hesseneck-Kailbach (DE); Stephan-Michael Frey, Griesheim (DE); Christian Hoerauf, Oftersheim (DE); Paul Patel, Sunnyvale, CA (US)

(73) Assignee: Roche Diabetes Care, Inc., Indianapolis, IN (US)

(*) Notice: Subject to any disclaimer, the term of this patent is extended or adjusted under 35 U.S.C. 154(b) by 97 days.

(21) Appl. No.: 13/873,046

(22) Filed: Apr. 29, 2013

(65) Prior Publication Data
US 2013/0237881 A1 Sep. 12, 2013

Related U.S. Application Data

(63) Continuation of application No. 12/582,277, filed on Oct. 20, 2009, now abandoned, which is a continuation of application No. PCT/EP2008/003355, filed on Apr. 25, 2008.

(60) Provisional application No. 60/914,897, filed on Apr. 30, 2007.

(51) Int. Cl.
*A61B 5/00* (2006.01)
*A61B 5/151* (2006.01)
(Continued)

(52) U.S. Cl.
CPC ............ *A61B 5/1519* (2013.01); *A61B 5/1411* (2013.01); *A61B 5/1459* (2013.01); *A61B 5/15142* (2013.01); *A61B 5/15186* (2013.01);
(Continued)

(58) Field of Classification Search
CPC ...................................... A61B 5/1519
USPC .................. 600/583, 584; 606/181–183; 204/403.03, 415
See application file for complete search history.

(56) References Cited

U.S. PATENT DOCUMENTS

| RE32,922 E | 5/1989 | Levin et al. |
| 5,318,584 A | 6/1994 | Lange et al. |

(Continued)

FOREIGN PATENT DOCUMENTS

| EP | 1245187 A1 | 10/2002 |
| EP | 1342448 A1 | 9/2003 |

(Continued)

*Primary Examiner* — Brian Szmal
(74) *Attorney, Agent, or Firm* — Harness, Dickey

(57) ABSTRACT

Instrument for producing a sample of body liquid for analysis by piercing the skin with a lancing element having a skin piercing tip. The instrument has a housing and a lancing drive for driving a lancing element connected thereto in a puncturing movement. A pressure ring surrounds a skin contact opening and is adapted for pressing against the skin such that the skin bulges into the opening for promoting expression of body fluid. The skin contact opening has an opening area corresponding to a circle with a diameter of at least 3 mm and at most 8 mm, and the instrument comprises a pressing force control device for controlling the pressing force between the pressure ring and the skin at the time of triggering the puncturing movement, to be at least 3 N and at most 8 N.

24 Claims, 3 Drawing Sheets

(51) Int. Cl.
 *A61B 5/15* (2006.01)
 *A61B 5/1459* (2006.01)
 *A61B 5/145* (2006.01)

(52) U.S. Cl.
 CPC ..... *A61B 5/14532* (2013.01); *A61B 2562/0295* (2013.01)

(56) References Cited

U.S. PATENT DOCUMENTS

| | | |
|---|---|---|
| 5,487,748 A | 1/1996 | Marshall et al. |
| 6,306,152 B1 | 10/2001 | Verdonk et al. |
| 6,332,871 B1 | 12/2001 | Douglas et al. |
| 6,561,989 B2 | 5/2003 | Whitson |
| 6,589,260 B1 | 7/2003 | Schmelzeisen-Redeker et al. |
| 6,749,618 B2 | 6/2004 | Levaughn et al. |
| 7,955,271 B2 | 6/2011 | Roe et al. |
| 2003/0143113 A2 | 7/2003 | Yuzhakov et al. |
| 2003/0191415 A1 | 10/2003 | Moerman et al. |
| 2003/0212344 A1 | 11/2003 | Yuzhakov et al. |
| 2004/0138588 A1 | 7/2004 | Saikley et al. |
| 2004/0215224 A1 | 10/2004 | Sakata et al. |
| 2005/0011759 A1 | 1/2005 | Moerman et al. |
| 2005/0177071 A1 | 8/2005 | Nakayama et al. |
| 2006/0036187 A1 | 2/2006 | Vos et al. |
| 2006/0155317 A1 | 7/2006 | List |
| 2007/0004990 A1 | 1/2007 | Kistner et al. |
| 2007/0016103 A1 | 1/2007 | Calasso et al. |
| 2007/0060842 A1 | 3/2007 | Alvarez-Icaza et al. |
| 2007/0060843 A1 | 3/2007 | Alvarez-Icaza et al. |
| 2007/0060844 A1 | 3/2007 | Alvarez-Icaza et al. |
| 2007/0293882 A1 | 12/2007 | Harttig et al. |
| 2008/0021494 A1 | 1/2008 | Schmelzeisen-Redeker et al. |
| 2008/0082023 A1 | 4/2008 | Deck et al. |
| 2008/0262387 A1 | 10/2008 | List et al. |
| 2009/0192409 A1 | 7/2009 | Wong et al. |
| 2009/0275860 A1 | 11/2009 | Nakamura et al. |
| 2011/0270129 A1 | 11/2011 | Hoerauf |

FOREIGN PATENT DOCUMENTS

| | | |
|---|---|---|
| EP | 1360933 A1 | 11/2003 |
| EP | 1362551 A1 | 11/2003 |
| EP | 1527737 A1 | 5/2005 |
| EP | 1586269 A1 | 10/2005 |
| EP | 1586270 A2 | 10/2005 |
| EP | 1669028 A1 | 6/2006 |
| EP | 1736100 A1 | 12/2006 |
| JP | 2002219115 A | 8/2002 |
| JP | 2007029417 A | 2/2007 |
| RU | 1827169 C | 7/1993 |
| WO | 9926539 A1 | 6/1999 |
| WO | 0172220 A1 | 10/2001 |
| WO | 0189383 A2 | 11/2001 |
| WO | 03009759 A1 | 2/2003 |
| WO | 03088835 A2 | 10/2003 |
| WO | 2004041088 A1 | 5/2004 |
| WO | 2004045375 A2 | 6/2004 |
| WO | 2005013824 A1 | 2/2005 |
| WO | 2005084530 A2 | 9/2005 |
| WO | 2005084545 A1 | 9/2005 |
| WO | 2005084546 A2 | 9/2005 |
| WO | 2006058654 A2 | 6/2006 |
| WO | 2006072004 A2 | 7/2006 |
| WO | 2006092309 A2 | 9/2006 |
| WO | 2006109452 A1 | 10/2006 |
| WO | 2007041355 A2 | 4/2007 |
| WO | 2007042137 A2 | 4/2007 |
| WO | 2008022755 A1 | 2/2008 |

Fig. 1
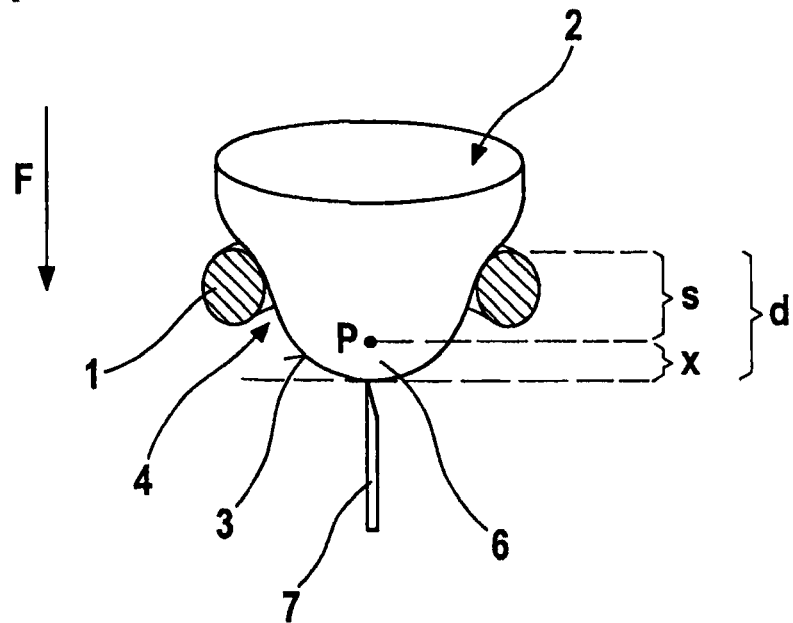
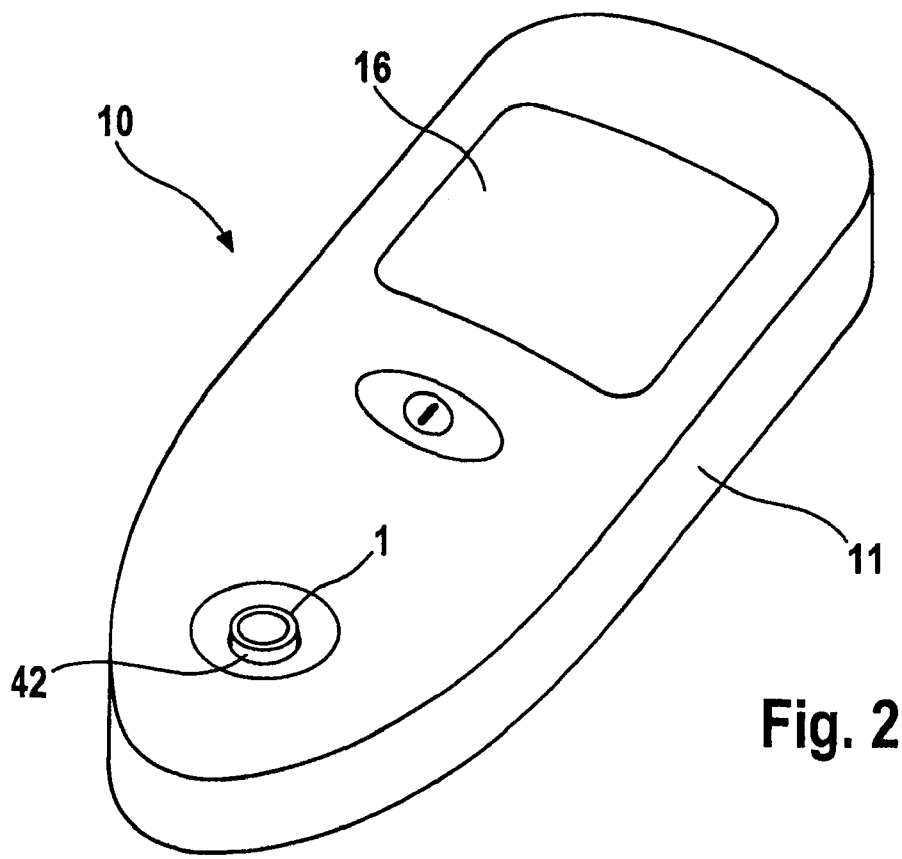
Fig. 2

INSTRUMENTS AND SYSTEM FOR PRODUCING A SAMPLE OF A BODY FLUID AND FOR ANALYSIS THEREOF

CROSS-REFERENCE TO RELATED APPLICATIONS

This application is a continuation of U.S. patent application Ser. No. 12/582,277, filed Oct. 20, 2009, which is a continuation of International Application No. PCT/EP2008/003355, filed Apr. 25, 2008, which claims the benefit of U.S. Provisional Application No. 60/914,897, filed Apr. 30, 2007. The entire disclosures of each of the above applications are incorporated herein by reference.

BACKGROUND

The invention relates to the collection of samples of body liquid for allowing analysis thereof, i.e. determination of an analyte concentration therein. In particular it relates to instruments and systems for producing a small sample of body liquid by piercing the skin of a subject (human or animal) using a disposable lancing element having a skin piercing tip suitable for generating a small wound from which the sample is drawn. Depending on the skin site used and on the lancing depth the body liquid is blood or interstitial liquid or a mixture thereof.

Analysis based on skin-piercing is important in several fields of medical diagnostics and treatment. Of particular importance is the field of diabetes management. It has been determined that severe long term damages caused by diabetes mellitus can be avoided if the patient controls her or his blood sugar level several times a day in order to adapt the required insulin injections closely to the actual need for maintaining a constant blood sugar level. This requires so called "home-monitoring" by the patient himself or by other people not having a medical training.

Other important fields of medical diagnostics and treatment with similar requirements, including home-monitoring, refer for example to the regular control of blood cholesterol and to the control of blood coagulation parameters. The invention is in particular suitable but not limited to home-monitoring applications. Similar requirements also exist, e.g., in so called "near-patient-testing".

Lancing of the skin is generally performed by a lancing system comprising, as mutually adapted components of the system, a reusable hand-held instrument and lancing elements. The movement required for lancing (puncturing movement) is driven by a lancing drive provided inside a housing of the instrument and adapted for driving a lancing element connected thereto. Lancets can be interchangeably connected to the drive and generally are disposable items.

After triggering the puncturing movement the lancet is driven in a puncture direction until it reaches a point of maximum displacement and thereafter it is further driven in a reverse direction. Many suitable lancet drive mechanisms have been described. In most cases the driving force is supplied by a tensioned spring and the lancet drive further includes suitable mechanical means for converting the force of the spring into the required movement of a lancet.

An important consideration in developing lancing systems is the pain caused by the pricking action. This pain and the convenience of use are decisive factors determining compliance of the patient, i.e. his willingness to perform regular analyses as required for maintaining his health. It has been determined that reliable production of the required amount of sample liquid with minimum pain highly depends on the reproducibility of an optimum penetration depth of the tip of the lancing element into the skin (see U.S. Pat. No. 5,318,584).

With earlier lancet systems the analysis generally required a plurality of steps to be performed by the user. After lancing with such earlier systems the blood did not readily emanate from the wound site in the lanced skin. Therefore manual "milking" steps such as pinching, squeezing and kneading where necessary in order to express the required amount of sample liquid. Finally sample liquid was contacted to an analysis element of an analysis system (which was separate and distinct from the lancing system) and the analysis was performed thereby.

In order to improve the production of sample liquid at the lancing site and to avoid the manual "milking" several proposals were made all of which relate to the design of the contact area at a distal end of the lancing instrument having a (generally ring-shaped) skin contact surface surrounding a skin contact opening. Such lancing systems are described in WO 99/26539, WO 01/89383 A2, EP 1 245 187 A1, EP 1 586 269, EP 1 586 270.

While these approaches differ in several ways, a common feature thereof is that the skin contact opening has a relatively large diameter whereby the skin bulges into the skin contact opening forming a target site bulge which penetrates to some extent into the opening when the lancing instrument is pressed with its distal end (i.e. with the skin contact surface) against the skin. This bulging action (hereafter designated "target site bulging") is generally combined with additional means for improving sample liquid production, such as a mechanical squeezing acting radially inwardly, a pumping action involving axial movement of parts of the instrument, etc.

Ideally these measures allow with a high success rate (preferably better than 90%) expression of a sufficient amount of sample liquid without manual "milking". This again is a requirement of integrated lancing and analysis systems which, in a single instrument, comprise both, means for the lancing-type sample production and means for the analysis. Such integrated systems have been proposed in a plurality of variants which can be assigned to two types, namely A) "Two unit systems" having—in a single instrument housing—two separate units for lancing and for analysis. Typically the units are moved one after the other to a common skin contact opening (see e.g. EP 1 669 028 A1 and EP 1 736 100 A1)

B) "Single unit systems" operating with a single combined lancing- and analysis unit suitable for performing both functions (lancing and analysis). Most such systems operate with integrated lancing and analysis elements. The two components of such combined lancing and analysis elements are generally manufactured separately but assembled by the manufacturer or at least before use, i.e. before the lancing movement is triggered. In the instrument such elements are processed as a unified item. In other single unit systems both functions (lancing and analysis) are performed by the same unit but a lancing element and an analysis element are provided and processed separately during at least a part of the analytical procedure. Examples of single unit systems are described in the following publications: WO 01/72220, WO 03/009759 A1, EP 1 342 448 A1, EP 1 360 933 A1, EP 1 362 551 A1.

Even though several of the discussed systems, in particular integrated lancing and analysis systems, provide improved results as compared to earlier known devices, there are still substantial shortcomings. There is a need for improvements with respect to several partially contradictory requirements including ease of use, minimum pain and minimum requirements concerning volume, weight and production cost.

SUMMARY

With a view to this aim a first aspect of the invention proposes an instrument and a system for producing a sample of body liquid by piercing the skin comprising
a housing
a lancing drive within said housing adapted for being connected to a lancing element and adapted for driving a lancing element connected thereto in a puncturing movement in which the lancing element moves, after triggering the puncturing movement, in a puncture direction until it reaches a point of maximum displacement and in a reverse direction after it has reached the point of maximum displacement,
a pressure ring surrounding a skin contact opening and being adapted for being pressed against the skin such that the skin bulges into the opening whereby expression of body fluid is promoted after the piercing tip of a lancing element has pierced the skin,
wherein the skin contact opening has an opening area corresponding to a circle with a diameter of at least 3 mm and at most 8 mm, and the instrument includes a pressing force control device for controlling the force acting between the pressure ring and the skin ("pressing force") at the time of triggering the puncturing movement, to be at least 3 N and at most 8 N.

This aspect of the invention relates to the target site bulging when a lancing instrument is pressed against the skin (or vice versa) at the lancing site. While this bulging is favorable regarding expression of a sufficient amount of sample liquid it causes a problem regarding reproducibility of the penetration depth by which the tip of the lancing element penetrates into the skin. With a given adjustment of the longitudinal position (i.e. position in the direction of the lancing movement; hereafter "z-position") of the lancing drive and consequently a given z-position of the point of maximum displacement of the lancet the penetration depth depends on the exact z-position of the skin surface during the puncturing movement. Due to the bulging this skin position is substantially undefined. It depends on a plurality of factors including not only differing skin elasticity of different users but also including changes of the (elastic and other) properties of the skin of a particular user caused by influencing factors such as temperature, previous skin treatment (e.g. washing with soap) and choice of the particular lancing site. Prior art approaches for overcoming this uncertainty about the skin position and the resulting uncertainty about the penetration depth include the following:
Detection of the exact z position of the skin by a skin position detection device integrated into the lancing instrument and operating for example by electric (capacitive) or optical detection means (WO 03/088835).
Providing in the instrument a penetration depth reference element having a reference skin contact surface which is contacted to the skin (additionally to the skin contact surface surrounding the skin contact opening of the instrument), for providing a reliable z position reference during penetration of the lancing element tip into the skin. Such a reference element can be moved towards the skin separately from the lancing element (EP 1 669 028 A1) or together therewith (WO2006/092309).

While these approaches help to achieve a reproducible penetration depth they require a substantial expense in the instrument design and production, making the system less handy and more costly. Therefore several of the lancing systems designed for target site bulging simply disregard the penetration depth uncertainty. This approach causes, however, a much larger pain than necessary, because it requires a high value of the penetration depth setting to make sure that a sufficient amount of sample liquid is produced even with a disadvantageous position of the lancing site bulge.

In the context of the invention it has surprisingly been found that an excellent reproducibility of the z-position of the skin bulge at the lancing site and thus an excellent reproducibility of the penetration depth can be achieved if particular conditions are ensured concerning the size of the skin contact opening and concerning the force by which the pressure ring and the skin are pressed against each other at the time of triggering the puncturing movement. This allows to use target site bulging and automatic sample generation (without "milking") combined with a simple and inexpensive design of the lancing system. The system works without a z-position detection means and without a penetration depth reference element adapted for contacting the skin which bulges into the pressure ring.

Generally the skin contact opening is circular and in this case it should have an inner (free) diameter of at least 3 mm, preferably at least 4 mm, more preferably at least 5 mm and most preferably at least 5.5 mm. The upper limit of the preferred range of diameter is 8 mm, preferably 7 mm, more preferably 6.5 mm and most preferably 6 mm. In case of a non-circular skin contact opening the area of the opening should correspond (i.e. be the same) as the area of a circle with the mentioned diameter values. However, in any case, the smallest inner (free) width of a non-circular skin contact opening should be at least 3 mm, preferably at least 4 mm.

The pressing force acting at the time of triggering the puncturing movement between the pressure ring and the skin should at least be 3 N, preferably 4 N and more preferably 5 N and it should at most be 8 N, preferably 7 N and more preferably 6 N. A defined pressing force within these limits is ensured by a suitable pressing force control device. Such a device can be mechanical, in particular comprising a spring device which is arranged in such a manner that its spring force acts between the pressure ring and the housing. The spring device is preferably embodied as a metal spring. Other spring-like devices are, however, known and can be used, such as a pneumatic spring or a resilient element of an elastic material. Hereafter the term "spring" is used as an example of any such spring device. Preferably is pre-tensioned, as will be described in more detail below.

Pressing force control devices operating by electrical means may comprise an electromagnetic drive including a coil and a magnetic core, in particular a voice coil drive. The control of the pressure can be fully automatic or it can require an activity of the user. In the latter case electrical means can be used to measure the force by which the pressure ring is pressed against the skin and this force can be indicated to the user by suitable visible, acoustic or tactile means, whereby the user can adapt the pressing force to the desired value.

According to a second aspect of the invention, which is preferably combined with the first aspect but can also be used independently, the invention proposes a system and an instrument for producing a sample of body liquid by piercing the skin using a lancing element having a skin piercing tip and for analysis using a disposable analysis element, said instrument having
a housing
a lancing drive within said housing adapted for being connected to a lancing element and adapted for driving a lancing element connected thereto in a puncturing movement in which the lancing element moves, after triggering the puncturing movement, in a puncture direction until it reaches a point of maximum displacement and in a reverse direction after it has reached the point of maximum displacement, a pressure ring surrounding a skin contact opening and being adapted for being pressed against the skin such that the skin bulges into the opening whereby expression of body fluid is promoted after the piercing tip of a lancing element has pierced the skin, and a holding device adapted for holding an analysis element in said housing such that a sample of body liquid produced by piercing the skin can be transported thereto for analysis, wherein a minimum interaction time period required for lancing and sampling a sufficient amount of sample liquid for analysis is at most 3 seconds. Preferably the minimum interaction time period is no more than 2 seconds and more preferably it is no more than 1 second.

This aspect of the invention specifically relates to integrated lancing and analysis systems of both types A and B identified above. In such systems the user interacts with the system by establishing a pressing force between the skin and the pressure ring of the instrument. This can conveniently be done by pressing a hand-held instrument against the finger or other body part. Alternatively the finger or other body part can be pressed against an instrument, lying e.g. on a table.

According to the prior art, timing has in this context generally been only a concern with respect to the "test time", i.e. the total time required for the analysis (from lancing until the analyte concentration is indicated). The inventors have found that—deviating from earlier understanding—the duration of the minimum interaction time period ("MITP") is highly critical for achieving the partially contradictory requirements mentioned above. This time period is defined as the minimum time duration for which user-instrument interaction (as specified above) is required for lancing and for collecting a sufficient amount of sample for the analysis in a sample collection device of the system. The functions performed during the MITP include lancing, expression of sample liquid from the tissue (preferably directly into a capillary of the lancing element) and collecting a sufficient amount of sample.

The MITP is a system-related quantity which is user-independent, i.e. only determined by the design of the instrument, and possibly by other components of the system. It must not be confused with the actual time of interaction which in each case depends on numerous aspects including the habits of the user. The actual interaction time generally varies between users and, even for a specific user, from analysis to analysis. The invention teaches to design the system in such a manner that the minimum time for which every user must at least interact with the instrument is below the indicated very small threshold values.

The starting point of the MITP is a point in time at which the system is "ready for lancing", i.e. the lancing drive is ready for driving a lancing movement of a lancing element connected thereto and the desired lancing site of the skin is properly located at the skin contact opening of the instrument. Depending on the design of the system a short period of time may be required between establishing the status "ready for lancing" and the triggering of the puncturing movement. Such a short (preparatory) delay period may be required by the instrument, for example for detecting the skin position. Preferably, however, the design is such that no such preparatory time period is needed due to instrumental requirements, i.e. the triggering can immediately take place when the status of the system is "ready for lancing". In this case the starting point of the MITP may coincide with the triggering of the puncturing movement.

A very short and well defined preparatory delay period may, however, be provided for non-instrumental reasons, in particular to take into account visco-elastic deformation of the skin which takes place after establishing a pressure force between the skin and the pressure ring.

The end of the MITP is marked by the fact that a sufficient amount of body liquid has been sampled, i.e. is available in the sample collection device of the instrument for analysis. A "sample collection device" as used herein is any part of the system, inside the instrument, in which sample liquid produced as a result of skin lancing is available for analysis. It can, for example, be a chamber or capillary and can be empty, or filled with bibulous material.

Details depend on the type and design features of the particular system.

In the case of a "two unit system" the sample collection device belongs to the analysis unit. It can be a part of an analysis element or of a dedicated sample collection element and collects sample after the analysis unit has been moved to the skin contact opening.

In the case of a "single unit system" the sample collection device can be a part of a lance element, a part of an analysis element, a part of an integrated lancing and analysis element or a part of a dedicated sample collection element.

If the sample collection device is a part of an analysis element or of an integrated lancing and analysis element it can, in particular, be a part of a reaction zone thereof containing reagents which react with the sample liquid, thereby producing some kind of measurable physical change which is characteristic for the analysis.

Preferably the sample collection device is separate from the reaction zone of the analysis element and includes a reservoir, which is suitable for storing a sample liquid for an intermediate storage time which is longer than the MITP. One advantage of this embodiment is that it allows to separate the timing requirements of the sample collection from the timing requirements of the analysis. The MITP is terminated as soon as the reservoir of the sample collection device contains a sufficient amount of sample liquid for the analysis. Further steps, including for example the filling of a reaction zone, can take place separately without continued interaction of the user.

In the last mentioned preferred embodiment the transfer of the sample liquid from the reservoir of the sample collection device to the reaction zone of the analysis element can either take place spontaneously or with controlled timing. In the former case permanent fluid communication is provided between the reservoir and the reaction zone. In the latter case the fluid communication from the reservoir of the sample collection device to the analysis element is "switchable", i.e. initially, preferably at least for the duration of the MITP, there is no fluid communication but same is established in a controlled manner at a suitable point of time. Suitable means for such switching are known for example from WO 2005/084546.

Preferably the instrument according to the second aspect of the invention comprises a pressing force control device which may be designed in the same manner as described above with respect to the first aspect of the invention. If both aspects are combined the instrument preferably has only one pressing force control device. However, deviating from the first aspect, here the value of the pressing force during the entire MITP is important. By means of the pressing force control device it should preferably be maintained to be at least 3 N, preferably at least 4 N and more preferably at least 5 N during the MITP. According to another preferred embodiment maximum values should be maintained during the same period, namely at most 10 N, preferably at most 8 N and more preferably at most 7 N.

These limiting values of the pressure force are preferred with respect to the requirements of withdrawing sample from the skin. However, this does not mean that the pressing force should be allowed to float in that range during the MITP. Rather it has been found that the maximum variation range of the pressing force should be limited to no more than 15%, preferably no more than 10% and more preferably to no more than 5%. Expressed in absolute values the maximum variation range of the pressing force between the pressure ring and the skin during the MITP should be no more than +/−0.5 N, preferably not more than +/0.3 N and more preferably not more than +/−0.2 N.

As noted above the MITP is a user-independent quantity which depends only on the design of the system. Preferably, however, the instrument comprises a MITP controlling device. This term refers to any device which helps to make sure that the required interaction between the user and the instrument (i.e. mainly the required pressing force between the skin and the pressure ring) is maintained by the user at least during the MITP. In other words the MITP controlling device provides assistance to make sure that the actual interaction between the user and the instrument overlaps (or at least coincides with) the MITP.

The MITP controlling device need not operate fully automatically in the sense that no acts of the user, such as manual triggering of the puncturing movement, are required. Rather it may provide assistance to the user, in particular by signaling to the user directly or indirectly the start and the end of the MITP.

The MITP controlling device comprises means for detecting the starting point of the MITP, by detecting the pressing force acting between a pressure ring and the skin using any suitable means (to be discussed in more detail below). When the pressure corresponds to a predetermined minimum value or range this status can be indicated to the user by a suitable visible, audible or tactile signal. Alternatively the lancing movement can be triggered automatically when the status "ready for lancing" has been detected. In this case there may be no delay between "ready to lance" and triggering, i.e. the MITP starts with the automatic triggering. Alternatively there may be an instrument-controlled delay time, e.g. to take into account the time needed for visco-elastic skin-deformation. In such cases the preparatory delay period between "ready to lance" and triggering is preferably at most 1 sec, more preferably at most 0.7 sec and most preferably at most 0.5 sec. A preferred lower limit is 0.2 sec, at least 0.3 sec being more preferred and at least 0.4 sec being most preferred.

The end of the MITP period is generally indicated to the user by a suitable visible, audible or tactile signal.

It should be noted, that a dedicated MITP controlling device is not necessary for the invention in its most general sense. Depending on the particular situation it may be sufficient for the user to be provided with an indirect indication of the start and end of the MITP. For example the "ready to lance"-status can be "felt" by the user when pressing his finger on a spring-supported pressure ring (to be described in more detail below) and the duration of the MITP may be so short, that it may be sufficient to rely on the "feeling" of the user with respect to the end of the MITP.

The instrument may have some kind of fill control (as part of the MITP controlling device) indicating a sufficient amount of sample liquid or allowing an analysis only if a sufficient amount of sample has been collected. However, in many cases such fill control is not required. Rather the end of the MITP is calculated by the instrument using a fixed MITP value (depending on the design of the system components).

In the context of the invention it has been found that substantial advantages are achieved with integrated lancing and analysis systems if the described pressing force between the pressure ring at the distal end of the lancing instrument and the skin is maintained not only at the time of lancing but also for a short interaction period thereafter:

With both types A and B of integrated lancing and analysis systems, maintaining this pressing force for a MITP helps to produce a sufficiently large volume of sample liquid.

In the case of type A (two unit systems) maintaining a MITP with the described pressing force is furthermore important to make sure that the position of the instrument (i.e. its skin contact opening) relative to the skin is fixed until the point of time that the analysis device is moved to the skin contact opening.

With systems of type B (single unit systems) it has been found that maintaining a MITP with the described pressing force is important in order to allow a precise z position of the lancing tip, thereby improving suctioning of a sufficient amount of sample liquid during a short period of time.

Furthermore it has been found in the context of the invention that many users of integrated lancing and analysis systems have problems to maintain a sufficient pressing force for a sufficient period of time and that compliance with recommended rules of using the instrument is much better with a system incorporating the features described here.

It has been found, that with suitable adaption of the minimum pressing force and (preferably) also of the upper limit of the pressing force, and (most preferably) the maximum variation range, advantageously combined with a size of the skin contact opening explained in the context of the first aspect of the invention, it is even possible and preferred to design the instrument with no user-setable penetration depth adjustment means. Surprisingly with a single factory-set z-position of the lancet drive (point of maximal displacement) and of the pressure ring, relative to each other, a reliable production of sample liquid is possible with very little pain. Simultaneously omission of a penetration depth adjustment device allows a simple, compact and inexpensive design of the instrument.

Even if a user-setable penetration depth adjustment device is provided, the invention allows to use a simple and inexpensive design thereof. For example in order to adapt for small remaining variations of the skin position it may be sufficient to provide interchangeable distance elements or pressure rings to allow a single adaption of the systems to the needs of a particular user.

In general the instrument and system of the invention take into account the viscoelastic properties of the skin in an optimized manner. In this way not only a sufficient supply of sample liquid is ensured but also "flooding" by too much sample liquid is avoided. The invention allows reliable analysis even with very small sample volumes in the order of less than 300 nl, preferably less than 200 nl.

DRAWINGS

The invention is hereafter described in more detail with reference to preferred embodiments shown in the drawings. The technical features and elements shown therein can be used individually or in combination to design embodiments of the invention. In the drawings FIG. 1 shows a schematic sketch relating to the principles of target site bulging;

FIG. 2 shows a perspective view of an analysis instrument;

DETAILED DESCRIPTION

Figure 3:
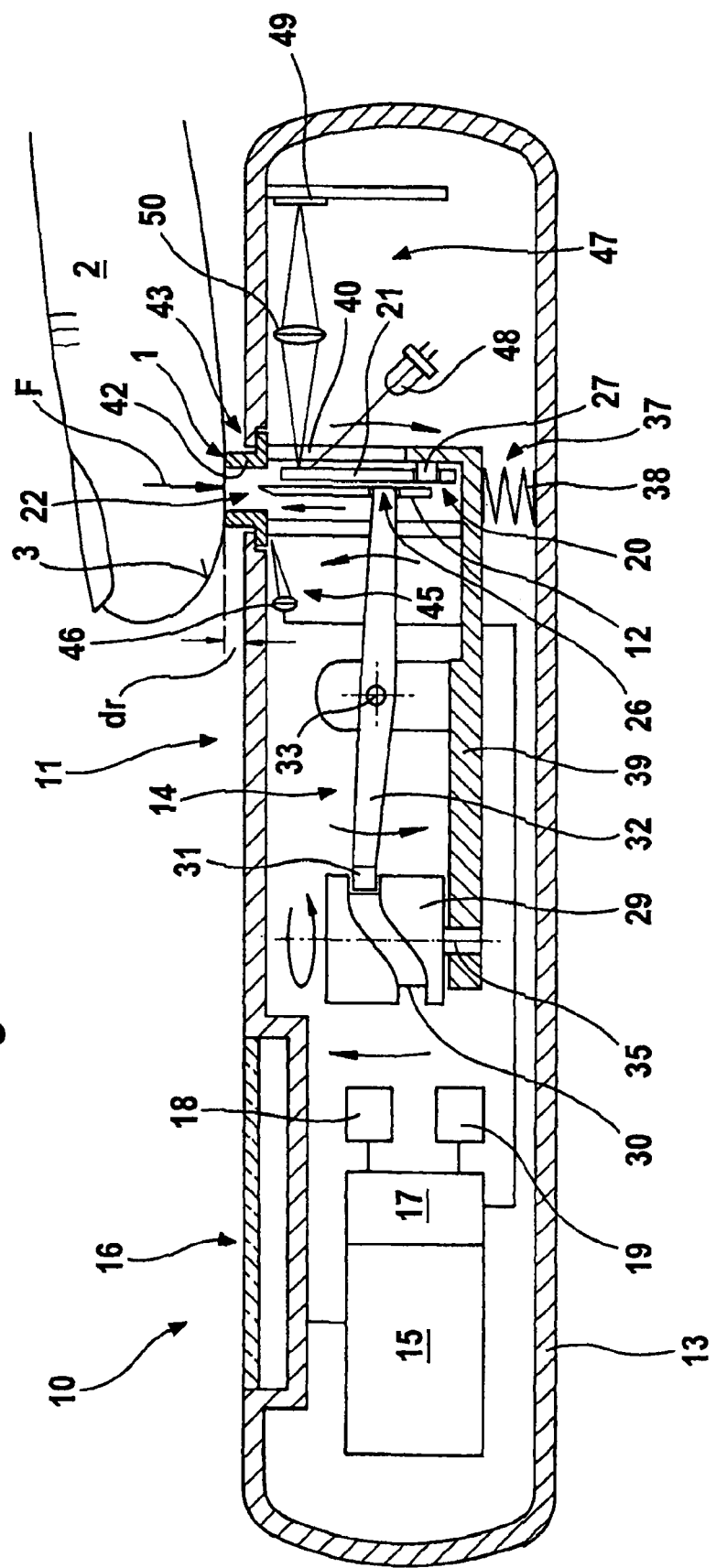
FIG. 3 shows a longitudinal section of the instrument shown in FIG. 2.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

FIG. 1 shows a view of a pressure ring 1 against which a fingertip 2 is pressed with force F. Due to this pressing force the skin 3 bulges into the skin contact opening 4 defined by pressure ring 1, forming a target site bulge 6.

The degree of such target site bulging, i.e. the distance d between the plane of pressure ring 1 and the apex of target site bulge 6 is influenced in a complicated manner by numerous factors including the size of the skin contact opening 4, the pressing force F and the viscoelastic properties of the skin. These again depend on a plurality of factors including the elasticity of the skin surface of the particular individual which largely differs depending on age, sex and degree of manual work generally performed by the particular person the internal pressure in the finger or other body part which depends among others on the health status and the physical activity of the particular person ambient conditions, including in particular temperature and humidity, influencing the viscoelastic properties of the skin skin treatment preceding the lancing, such as washing with soap, disinfecting, etc.

FIG. 1 also shows symbolically the point P of maximum displacement which a piercing tip 7 reaches on its movement path during the puncturing movement. With most lancing instruments the z-positions of the plane of the pressure ring 1 and the point of maximum displacement P relative to each other (i.e. distance s shown in FIG. 1) can be adjusted in order to allow a penetration depth setting. FIG. 1 clearly shows that for a given value of this adjustment the actual penetration depth x depends directly on the distance d, i.e. the degree of target site bulging.

As noted above, in the prior art this uncertainty about the actual z position of the skin (i.e. the apex of the target site bulge) has either been disregarded or has been taken into account by measuring or referencing the actual skin position. In the context of the invention it has surprisingly been found that a very good reproducibility of the penetration depth during lancing can be achieved if the above specified conditions concerning the area of the skin contact opening and the amount of the pressing force are maintained.

FIGS. 2 to 5 show a suitable lancing system 10. It includes a reusable hand-held instrument 11 and a disposable lancing element 12 with a piercing tip 7. A housing 13 of the instrument contains a lancing drive 14 and a measurement and evaluation electronics 15 shown only symbolically as a block in FIG. 3. A display 16 is provided in order to allow visual indication of information (including status information concerning the system, advice concerning its handling, analytical results etc.) to the user. Optionally the instrument also comprises a MITP controlling device 17, a device 18 for generating audible signals (such as a buzzer) and/or a device 19 for generating tactile signals (such as a vibration generator).

In a preferred embodiment (best shown in FIG. 4) lancing element 12 is combined with an analysis element 21, thereby forming an integral lancing and analysis element 22. In this integral element the lancing element 12 is movable in a longitudinal direction symbolized by double arrow 34. An analysis element holder 20 is provided for holding the analysis element 22 inside the instrument 11. In the embodiment shown analysis element holder 20 comprises a coupling recess 25 in analysis element 21 and a corresponding coupling protrusion 27 of the instrument. In a similar manner the lancing element 12 has a coupling recess 24 cooperating with a coupling protrusion 26 of the instrument. These pairs of recesses 24,25 and protrusions 26,27 penetrating into the respective coupling recesses allow the handling of an integral lancing and analysis element 22 which has been inserted into the instrument (FIG. 3).

The lancet drive 14 shown in FIG. 3 comprises a drive rotor 29 with a cam 30 formed by a groove. Cam 30 and a corresponding cam traveler 31 form a cam drive mechanism which controls a pivoting movement of a drive rod 32 about a pivoting axis 33.

After triggering of a puncture movement (by triggering means not shown) drive rotor 29 turns with high speed (driven by a drive spring also not shown) about its axis 35 and this rotational movement is translated by means of the cam curve formed by groove 30 and traveled by cam traveler 31 into a corresponding pivoting movement of drive rot 32 which again drives a corresponding up and down movement of lancing element 12 to which it is connected by its coupling protrusion 26 penetrating into coupling recess 24. Similar rotor drives for lancing instruments have been described elsewhere. Thus no more detailed description is necessary.

Figure 4:
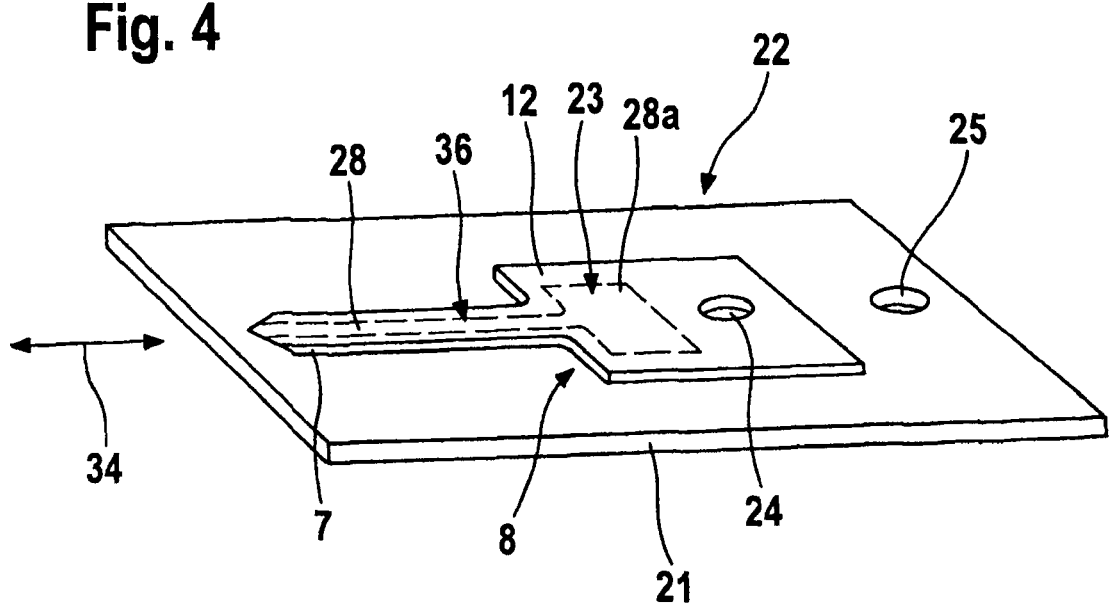
FIG. 4 shows a perspective view of a lancing element for use in the instrument shown in FIG. 3.

In the preferred embodiment shown in FIG. 4 the lancing element 12 is a "direct sampler" having a capillary channel 28 inside its piercing tip 7 and leading up to a sample collection zone 23 of lancing element 12. In sample collection zone 23 capillary channel 28 widens to form a sample reservoir chamber 28a.

During lancing, lancing element 12 performs a puncturing movement by which piercing tip 7 is driven into skin 3. Thereafter, preferably during a retraction phase of the puncturing movement, after the piercing tip 7 has reached its point of maximum displacement (but with the piercing tip still being below the surface of skin 3) sample liquid penetrates—driven by capillary forces—into capillary 28 and reservoir chamber 28a. Thus, in the embodiment shown, capillary 28 and reservoir chamber 28a together form a sample collection device 36 suitable for storing sample liquid, ready for subsequent transfer to an analysis zone 8 of analysis element 21.

Once sample liquid has arrived at sample collection zone 23 it may be transferred to the adjacent analysis zone 8 of analysis element 21 by means of a suitable fluid communication device. Preferably the arrangement is such that in a first configuration no fluid communication between the sample collection zone of lancing element 12 and the analysis element 21 is provided whereas in a second configuration fluid communication takes place. The switching between both configurations can be accomplished by any suitable means, e.g. by pressing zone 23 of lancing element 12 and analysis element 21 together. A more detailed description of such preferred design of an integrated lancing and analysis element with switchable sample transfer is not necessary because it has been described elsewhere.

Of course the invention can also be used with integral lancing and analysis elements having a lancing part and a analysis part fixed to each other. Evidently with such an embodiment no separate holding devices for the two parts are required. Rather only one holding device is provided which simultaneously serves as lancing element holding device and as analysis element holding device.

While preferred devices for holding and moving a lancing element and an analysis element (or an integral lancing and analysis element) in the instrument have been described, many variants are possible. These include a design in which analysis elements and/or lancing elements are fixed to and transported by means of a tape during at least a part of the system operation.

A special feature of the system of the invention relates to a pressing force control device 37 provided in the instrument 11. In the embodiment shown the pressing force control device 37 comprises a spring 38 which is embodied and arranged in such a manner that one end thereof acts against pressure ring 1 and the other end acts against the housing 13. "Acting" in this context does not require immediate contact. Rather it means that the spring exerts a force on the pressure ring and that the corresponding counter-force is (directly or indirectly) borne by the housing.

In the instrument shown in FIG. 3 one end of spring 38 rests on a wall of housing 13 and its other end presses against a frame element 39 carrying lancing drive 14. The force of spring 38 is further transmitted from the frame element 39 to pressure ring 1 via pillar elements 40. Pressure ring 1 is embodied as part of a pressure piece 42 which is borne by a pressure ring bearing 43 of housing 13 such that it is axially movable against the force of spring 38.

When a user presses her or his fingertip 2 in the direction of arrow F onto pressure piece 42 with pressure ring 1, the latter moves downwardly against the force of spring 38 (or other spring device). As soon as the contact between pressure piece 42 and the housing 13 at pressure ring bearing 43 is interrupted, the force of spring 38 is balanced by the pressing-down force of the finger. In other words the force by which the pressure ring 1 is pressed against the skin is in this status controlled by the pressing force control device 37, embodies here by means spring 38.

Figure 5:
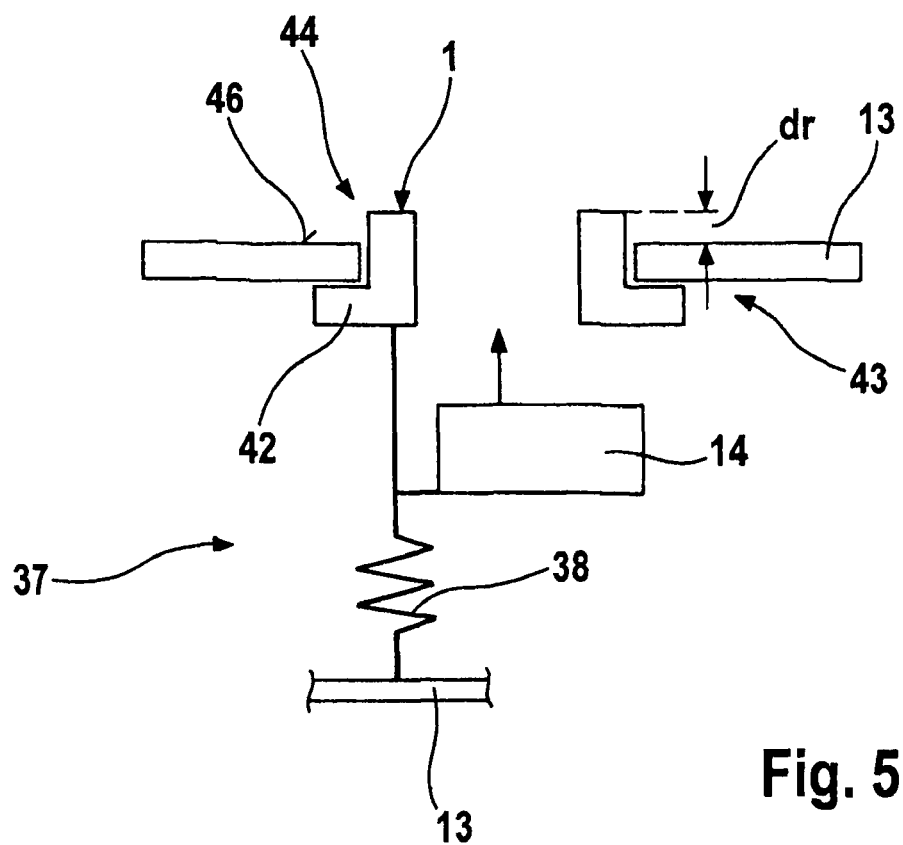
FIG. 5 shows a schematic sketch regarding an aspect of the function of the instrument shown in FIG. 3.

The principles used in this design are more clearly apparent from FIG. 5 showing that spring 38 acts between housing 13 and pressure piece 42 with pressure ring 1. Drive 14 is connected in a defined spatial configuration with pressure ring 1, in such a manner that the distance between the point of maximum displacement of the lancet movement and the pressure ring 1 is independent from the compression status of the spring 38 and the corresponding axial movement of pressure piece 42. Preferably the spatial configuration and hence the distance of the pressure ring from the point of maximum displacement can be varied (between puncturing movements) to set the lancing penetration depth. It is, however, fixed during the interaction of the user with the device, i.e. from the point of time at which the pressure ring is first pressed down until the body part is removed therefrom.

As is well known the force of an elastic spring 38 increases linearly with its elongation (i.e. compression in the case of a compression spring as shown). In the context of the invention the force by which the pressure ring 1 is pressed against the skin shall be controlled closely, i.e. the variation thereof should not exceed the preferred limiting values given above. In order to achieve this end, spring 38 is preferably embodied and arranged in such a manner that it is pre-tensioned. This means that the spring is already compressed (or in the case of an extension spring extended) even is no pressing force is exerted onto pressure ring 1, i.e. pressure ring 1 is in its "home" position resting on the surrounding wall (bearing 43) of housing 13. The degree of this pre-tensioning is such that the force of spring 38 acting on the pressure ring 1 varies by no more than 20%, preferably no more than 10% within the spring-loaded movement range of the pressure ring 1.

In this context it is important to make sure, that in the entire movement range the pressing-force acting between the finger 2 (or other body part) and the pressure ring 1 is controlled only by the force of spring 38 balanced by the pressing-down-force of finger 2. This condition would not be met if the movement of pressure ring 1 was influenced or limited by some kind of abutting member or obstacle acting—within its possible movement range—on ring 1. In order to meet this condition a pressure ring movement limiting arrangement 44 (FIG. 5) is provided by which the maximum displacement of the pressure ring 1 possible by pressing with a finger 2 or other body part is limited within a fully spring-loaded movement range of the pressure ring.

In the preferred embodiment shown in FIG. 5 this is achieved by a contact surface 46 which is arranged in the vicinity (at the outer side) of the pressure ring 1 in such a manner that a body part pressed against the pressure ring 1, and thereby moving the pressure ring, abuts against the contact surface 46. Due to this abutting, the pressure ring cannot be moved further, i.e. the possible displacement of the pressure ring (by the body part pressing thereagainst) is limited. With such an embodiment the maximum displacement depends on the distance dr by which the pressure ring protrudes from the instrument housing (contact surface 46). When pressure piece 42 with pressure ring 1 is pressed downwardly this movement is discontinued when fingertip 2 contacts the surface of housing 13 in the vicinity of the pressure ring 1.

In this context it is also favorable if the design is such that the maximum displacement of the pressure ring 1 during practical use is small. Preferably it should be less than 3 mm, more preferably less than 2 mm and even more preferably less than 1 mm. Therefore the distance dr of the plane of pressure ring 1 and the adjacent housing surface should not be too large. Preferred maximum values can be calculated by adding 0.5 mm to the mentioned maximum displacement values. On the other hand, distance dr should not be too small, among others because it is favorable for the handling of the instrument if a protrusion of pressure ring 1 versus the adjacent housing area simplifies the finding of a suitable finger position for the user. Therefore this protrusion, i.e. the distance dr, should be at least 0.2 mm, and preferably at least 0.5 mm.

In contrast to some earlier devices pressure ring 1 should be non-deformable in the sense that it should not be visibly deformed during normal use of the system. A suitable exact shape and width of the pressure ring can be determined experimentally. According to the present knowledge of the inventors it should preferably have a width of at most 3.5 mm, preferably at most 2.5 mm and more preferably at most 1 mm. A preferred minimum width is 0.5 mm, preferably 0.7 mm and more preferably 0.8 mm. The ring should protrude from any adjacent housing surface by a sufficient distance to allow easy tactile recognition thereof by the user.

Of course the construction part at which the pressure ring is provided can have many different shapes and designs. The term "pressure ring" refers to the ring-shaped surface of the respective part which in practical use, i.e. under the conditions prevailing in using of the particular instrument) contacts the skin surface. Of course this ring-shaped contact surface (i.e. the pressure ring) can have varying shapes including e.g. slightly rounded edges.

Furthermore the term "pressure ring" does not have to be understood as being limited to an uninterrupted ring. Rather the ring shaped surface contacting the skin can have interruptions (for example by recesses) which should, however, be small enough not to spoil the described function of the pressure ring.

In the preferred embodiment shown in FIG. 3 the instrument furthermore comprises a pressure-ring-movement detection device 45. In the context of the second main aspect of the invention it is preferably a part of a MITP control device. Means for movement detection are well known, for example a light barrier 46 as shown symbolically in the drawing. Such a device detects the movement of pressure piece 42, and hence of pressure ring 1, upon pressing down from its "home" position by finger 2. Such detection allows several favorable functions including an indication to the user (via display 16 or generators of audible or tactile signals 18 and 19) that the instrument is "ready for lancing". Alternatively or additionally the signal of the pressure-ring-movement detection device can be used for automatically triggering the lancing movement, possibly after a delay time as described above.

FIG. 3 furthermore shows an analysis measurement device 47 as part of the instrument 11. This can be any device which is suitable to measure a value of a measurement quantity relating to a change of analysis element 21, which change is a measure of the desired analytical value. In the case shown, the analysis measurement device is embodied for a photometric measurement of a detection area in the analysis zone 8 of analysis element 21 including a light source 48, a light detector 49 and corresponding light guide means symbolized by a lens 50. Other types of analysis measurement devices could be used as well, in particular electrical measurement devices, as are common for the evaluation of electrochemical analysis elements.

In the system shown in FIGS. 2 to 5 a MITP control device 17 in accordance with the second main aspect of the invention makes use of the pressure-ring-movement detection device 45. Once MITP control device 17 signals the start of an MITP it generates a signal by at least one of signal generators 18 and 19 and/or automatically triggers a puncturing movement of lancet drive 14. The end of the MITP period is determined by the measurement and evaluation electronics 15, for example on the basis of a predefined time period required for generation and transfer of sufficient amount of sample liquid from the fingertip 2. Alternatively the status of a sufficient sample transfer may be separately detected by suitable sample transfer detection means as are known in the art, e.g. photometric detection of the sample transported in the integral lancing and analysis element 22 or by electrical contacts detecting that sample liquid transported therein has reached a certain point in its transport path. Preferably—as in the embodiment shown—the application force control device makes sure that during the entire MITP the pressing force is within the range given by the above identified limiting values. Preferably the variation of the pressing force during the MITP should be within the above identified variation limitations which are much smaller.

What is claimed is:

1. An instrument for producing a body fluid sample for analysis by piercing skin with a lancing element having a piercing tip, the instrument comprising:
    a housing;
    a lancing drive within the housing for driving a lancing element connected thereto in a puncturing movement in which the lancing element moves, after triggering the puncturing movement, in a puncture direction until the lancing element reaches a point of maximum displacement and in a reverse direction after the lancing element has reached the point of maximum displacement;
    a pressure ring configured to be pressed against the skin such that the skin bulges into a skin contact opening for promoting expression of body fluid, wherein the pressure ring defines an opening area corresponding to a circle with a diameter of at least 3 mm and at most 8 mm; and
    a pressing force control device for controlling a pressing force between the pressure ring and the skin at the time of triggering the puncturing movement, wherein the pressing force at the time of triggering is at least 3 N and at most 8 N,
    wherein the instrument works without a z-position detection means and without a penetration depth reference element configured for contacting the skin that bulges into the pressure ring.

2. The instrument according to claim 1, wherein the pressure ring defines an opening area corresponding to a circle with a diameter of at most 6 mm.

3. The instrument according to claim 2, wherein the pressure ring defines an opening area corresponding to a circle with a diameter of at most 5 mm.

4. The instrument according to claim 1, wherein the pressing force is at least 4 N and at most 7 N.

5. The instrument according to claim 1, further comprising a holding device for holding an analysis element in the housing such that the body fluid sample produced by piercing the skin can be transported thereto for analysis.

6. The instrument according to claim 1, wherein the instrument comprises a device for automatically triggering the puncturing movement when the pressing force corresponds to a value of at least 3 N; and
    the instrument provides a minimum interaction time period of at most 3 seconds, starting from the triggering of the puncturing movement, for which every user must at least interact with the instrument by a pressing force between the skin and the pressure ring for lancing, expression of sample liquid from the tissue, and collecting an amount of sample liquid for analysis.

7. The instrument according to claim 1, wherein the pressing force at the time of triggering is at least 5 N.

8. An instrument for producing a body fluid sample by piercing skin and for analyzing the body fluid sample, the instrument comprising:
    a lancing element having a piercing tip;
    a sample collection device for collecting an amount of body fluid sample required for analysis;
    a disposable analysis element;
    a housing;
    a lancing drive within the housing connected to the lancing element and for driving the lancing element connected thereto in a puncturing movement in which the lancing element moves, after triggering the puncturing movement, in a puncture direction until the lancing element reaches a point of maximum displacement and in a reverse direction after the lancing element has reached the point of maximum displacement;
    a pressure ring configured to be pressed against the skin such that the skin bulges into a skin contact opening for promoting expression of body fluid;
    a holding device for holding the disposable analysis element in the housing such that the body fluid sample is transported thereto from the sample collection device for analysis; and
    a pressing force control device that controls a pressing force between the pressure ring and the skin, and a device for automatically triggering the puncturing movement when the pressing force corresponds to a value of at least 3 N, and wherein the instrument provides a minimum interaction time period of at most 3 seconds, starting from the automatic triggering of the puncturing movement, for which every user must at least interact with the instrument by the pressing force between the skin and the pressure ring of the instrument for lancing, expression of sample liquid from the tissue and collecting an amount of sample liquid for analysis.

9. The instrument according to claim 8, wherein the minimum interaction time period is not more than 2 seconds.

10. The instrument according to claim 8, wherein the pressing force control device comprises a spring device arranged such that one end of the spring device acts against the pressure ring and the other end of the spring device acts against the housing.

11. The instrument according to claim 10, wherein the spring device is pre-tensioned such that the force of the spring device acting on the pressure ring varies by not more than 20% within the spring-loaded movement range of the pressure ring.

12. The instrument according to claim 10, wherein the lancet drive is connected with the pressure ring in a defined spatial configuration, such that the distance between the point of maximum displacement of the lancet movement and the pressure ring is independent from the compression status of the spring device and from the axial movement position of the pressure ring.

13. The instrument according to claim 10, further comprising, a pressure ring movement limiting arrangement, by which the maximum displacement of the pressure ring is limited within a spring-loaded movement range of the pressure ring.

14. The instrument according to claim 13, wherein the pressure ring movement limiting arrangement comprises a contact surface in the vicinity of the pressure ring, configured such that when a body part is pressed against the pressure ring and thereby moves the pressure ring, the body part abuts against the contact surface.

15. The instrument according to claim 8, wherein the pressure ring has a mean width of at least 0.5 mm and at most 3.5 mm.

16. The instrument according to claim 8, wherein the device for automatically triggering the puncturing movement triggers the puncturing movement when the pressing force corresponds to a value of at least 5 N.

17. The instrument according to claim 8, wherein the pressure ring defines an opening area corresponding to a circle with a diameter of at least 3 mm.

18. The instrument according to claim 8, wherein the pressure ring defines an opening area corresponding to a circle with a diameter of at most 6 mm.

19. The instrument according to claim 8, wherein the pressure ring defines an opening area corresponding to a circle with a diameter of at most 5 mm.

20. A lancing system for producing a body fluid sample analysis by piercing the skin, the system comprising:
a reusable hand-held-instrument comprising,
a housing;
a lancing drive within the housing connected to a lancing element and for driving a lancing element connected thereto in a puncturing movement in which the lancing element moves, after triggering the puncturing movement, in a puncture direction until the lancing element reaches a point of maximum displacement and in a reverse direction after the lancing element has reached the point of maximum displacement;
a pressure ring configured to be pressed against the skin such that the skin bulges into a skin contact opening for promoting expression of body fluid, wherein the pressure ring defines an opening area corresponding to a circle with a diameter of at least 3 mm and at most 8 mm;
a pressing force control device for controlling a pressing force between the pressure ring and the skin at the time of triggering the puncturing movement, wherein the pressing force is at least 3 N at the time of triggering;
a holding device for holding an analysis element in the housing such that a body fluid sample is transported thereto from the sample collection device for analysis; and
a lancing element interchangeably connected to the drive of the instrument,
wherein the instrument works without a z-position detection means and without a penetration depth reference element configured for contacting the skin that bulges into the pressure ring.

21. The lancing system according to claim 20, wherein the lancing element is a part of an integral lancing and analysis element.

22. The lancing system according to claim 20, wherein the lancing element is a direct sampler having a capillary channel for transporting the body fluid produced by piercing the skin by capillary flow to a sample collection zone thereof.

23. The lancing system according to claim 20, further comprising, a fluid communication device configured such that body fluid sample can be transferred from a sample collection zone of the lancing element to the analysis element for analysis.

24. The lancing system according to claim 20, wherein the hand-held-instrument comprises a device for automatically triggering the puncturing movement when the pressing force corresponds to a value of at least 3 N; and the hand-held-instrument provides a minimum interaction time period of at most 3 seconds, starting from the triggering of the puncturing movement, for which every user must at least interact with the hand-held-instrument by a pressing force between the skin and the pressure ring for lancing, expression of sample liquid from the tissue, and collecting an amount of sample liquid for analysis.

* * * * *